US009217712B2

(12) United States Patent
Mitsuyama et al.

(10) Patent No.: US 9,217,712 B2
(45) Date of Patent: Dec. 22, 2015

(54) METHOD FOR ASSISTING JUDGMENT OF ABNORMALITY OF REACTION PROCESS DATA AND AUTOMATIC ANALYZER

(75) Inventors: Satoshi Mitsuyama, Tokyo (JP); Yuki Fukuyama, Tokyo (JP); Hidekatsu Takada, Iruma (JP); Hideyuki Ban, Kodaira (JP); Tomonori Mimura, Kasama (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 893 days.

(21) Appl. No.: 12/995,219

(22) PCT Filed: May 28, 2009

(86) PCT No.: PCT/JP2009/059760
§ 371 (c)(1),
(2), (4) Date: Feb. 4, 2011

(87) PCT Pub. No.: WO2009/145251
PCT Pub. Date: Dec. 3, 2009

(65) Prior Publication Data
US 2011/0125415 A1    May 26, 2011

(30) Foreign Application Priority Data

May 30, 2008    (JP) .................................. 2008-141861
Apr. 8, 2009    (JP) .................................. 2009-094057

(51) Int. Cl.
*G06F 19/00*    (2011.01)
*G01N 35/00*    (2006.01)
(Continued)

(52) U.S. Cl.
CPC .......... *G01N 21/77* (2013.01); *G01N 35/00603* (2013.01)

(58) Field of Classification Search
CPC ......................... G01N 21/77; G01N 35/00603
USPC ........................................... 702/25; 422/82.05
See application file for complete search history.

(56) References Cited

U.S. PATENT DOCUMENTS

| 5,759,424 | A | 6/1998 | Imatake et al. |
| 7,307,718 | B2 * | 12/2007 | Moran et al. .................. 356/300 |
| 2009/0017544 | A1 * | 1/2009 | Iguchi et al. .................... 436/50 |

FOREIGN PATENT DOCUMENTS

| CN | 1540314 | 10/2004 |
| EP | 1772736 A1 * | 4/2007 |

(Continued)

OTHER PUBLICATIONS

Office Action issued in Japanese Patent Application No. 2013-168427 on Sep. 16, 2014.

*Primary Examiner* — Janet Suglo
*Assistant Examiner* — Yaritza H Perez Bermudez
(74) *Attorney, Agent, or Firm* — Baker Botts L.L.P.

(57) ABSTRACT

In the event of a suspected abnormality in the device, sample or reagent, a laboratory technician had to examine the abnormal reaction process data item by item, and infer the cause of the abnormality, which took effort and time in some cases. Abnormality judgment is assisted using: indicator computation means that computes an indicator indicating a feature parameter of a given waveform by applying a pre-defined evaluation formula to time series data of photometric values; relative indicator computation means that computes a value indicating a relationship of the indicator of target data to the indicator computed in the past; and indicator display means that simultaneously displays a value computed by the indicator computation means and the value computed by the relative indicator computation means. According to the present method, which is a method for assisting judgment of abnormality wherein a feature parameter of a given absorbance change is computed, it can be made easier to find certain abnormalities, and it becomes possible to attain more efficient device maintenance and improved device reliability without the addition of any new parts.

6 Claims, 10 Drawing Sheets

(51) Int. Cl.
  *G01N 21/00*  (2006.01)
  *G01N 21/77*  (2006.01)

(56) References Cited

FOREIGN PATENT DOCUMENTS

| JP | S59-142424 A | 8/1984 |
| JP | 63-101734 | 5/1988 |
| JP | H08-106992 A | 4/1996 |
| JP | H10-062271 A | 3/1998 |
| JP | 2000-039400 | 2/2000 |
| JP | 2003-247937 | 9/2003 |
| JP | 2004-347385 | 12/2004 |
| JP | 2004347385 A * | 12/2004 |
| JP | 2005-249783 | 9/2005 |
| JP | 2006-023214 | 1/2006 |
| JP | 2007-198739 | 8/2007 |
| JP | 2007-248089 | 9/2007 |

* cited by examiner

| Sample | Reagent | | Wavelength | Photometric time point | | | |
|---|---|---|---|---|---|---|---|
| | | | | 22 | 23 | 24 | ... |
| A | $R_A1$ | $R_A2$ | $\lambda_1$ | -3.58 | 1.33 | -5.45 | ... |
| | $R_A1$ | $R_A2$ | $\lambda_2$ | -2.72 | 1.95 | -7.55 | ... |
| B | $R_A1$ | $R_A2$ | $\lambda_1$ | -6.28 | 9.84 | -7.02 | ... |
| | $R_A1$ | $R_A2$ | $\lambda_2$ | -5.98 | 7.74 | -3.31 | ... |
| C | $R_A1$ | $R_A2$ | $\lambda_1$ | 3.66 | -4.15 | -2.23 | ... |
| | $R_A1$ | $R_A2$ | $\lambda_2$ | 5.18 | -5.39 | -1.62 | ... |

METHOD FOR ASSISTING JUDGMENT OF ABNORMALITY OF REACTION PROCESS DATA AND AUTOMATIC ANALYZER

TECHNICAL FIELD

The present invention relates to a technique and an automatic analyzer for measuring the concentration and activity value of a component of interest in a sample, as well as to software and a system that utilize the data from the measurement.

BACKGROUND ART

An automatic analyzer is a device that causes a chemical reaction by dispensing a sample and a reagent into a cell, measures the absorbance of this mixture, calculates the amount of change in absorbance and/or the rate of change in absorbance based on time series data of absorbance caused by the chemical reaction (hereinafter referred to as reaction process data), and computes the concentration and/or activity of a component of interest in the sample.

Such automatic analyzers are used in biochemical tests, immunological tests, etc., mainly at medical facilities. Results of such tests play an extremely important role when doctors make various diagnoses such as learning about a patient's disease condition, assessing the effects of treatments, catamnestic monitoring, etc. As such, with respect to analyses using automatic analyzers, techniques for guaranteeing that measurements were taken properly are crucial.

As one such method for guaranteeing measurement results, there is abnormality detection using reaction process data. This is a method of guaranteeing measurement results by judging the presence/absence of any abnormal change in absorbance appeared in the reaction process data. Thus, if it is judged that there is an abnormal change in absorbance, it would signify that some abnormality had occurred in the device, sample or reagent at the time of measurement, thereby precluding any guarantee of the measurement results. Consequently, the user would have to stop the analysis, find the cause of the abnormality, and take countermeasures.

As conventional art for such detection of an abnormality in reaction process data, with the "automatic chemical analyzer" disclosed in JP Patent Publication (Kokai) No. 63-101734 A (1988), there is disclosed a technique wherein a photometric time point at which there is a change exceeding a pre-defined threshold is detected with respect to reaction process data for a not-for-measurement wavelength for which absorbance does not vary as a function of the chemical reaction states of a sample and a reagent, and wherein the change in absorbance at the detected photometric time point is corrected with respect to a for-measurement wavelength.

PRIOR ART DOCUMENTS

Patent Documents

Patent Document 1: JP Patent Publication (Kokai) No. 63-101734 A (1988)

SUMMARY OF THE INVENTION

Problems to be Solved by the Invention

However, with the technique disclosed in JP Patent Publication (Kokai) No. 63-101734 A (1988) mentioned above, the presence/absence of an overall abnormality in the reaction process data is judged, and it was thus not necessarily easy to identify the various kinds of abnormality that occur due to the device, sample, reagent, etc. As such, in the event of a suspected abnormality in the device, sample or reagent, a laboratory technician had to examine the abnormal reaction process data item by item, and infer the cause of the abnormality, which took effort and time in some cases.

An object of the present invention is to provide a method addressing the problems above, wherein a given change in absorbance appeared in reaction process data is analyzed to assist in abnormality detection.

Means for Solving the Problems

The problems above may be solved through a method for assisting judgment of abnormality comprising: an indicator computation means that applies a pre-defined evaluation formula to time series data of photometric values to compute an indicator indicating a feature parameter of a given waveform; a relative indicator computation means that computes a value indicating a relationship of the indicator of target data with respect to the indicator computed in the past; and an indicator display means that simultaneously displays a value computed by the indicator computation means and the value computed by the relative indicator computation means.

In addition, the problems above may be solved through a method for assisting judgment of abnormality comprising: a reaction change component estimation means that estimates a photometric value change component caused by a chemical reaction; and a disturbance change component extraction means that computes a difference between the time series data and an estimated value obtained at the reaction change component estimation means, and extracts time series data of change components caused by a disturbance, wherein the indicator computation means performs processing using the time series data obtained at the disturbance change component extraction means. And this can be done while further enhancing the reliability of the judgment results since it is possible to dramatically reduce the influence of the absorbance change caused by the chemical reaction.

In addition, the problems above may be solved through a method for assisting judgment of abnormality comprising: the indicator computation means; a frequency distribution generation means that generates a frequency distribution for the indicator over a given period; and a frequency distribution difference presenting means that presents a difference in period for a given abnormality occurrence frequency using frequency distributions of two periods, namely at a time point of interest, and a time point preceding the time point of interest.

Effects of the Invention

Through a method for assisting judgment of abnormality that computes a feature parameter of a given change in absorbance, it is possible to make it easier to find certain abnormalities. It is possible to narrow down the abnormality occurrence site in the device, and device abnormality can thus be found quickly. In addition, through a method for assisting judgment of abnormality that presents an abnormality occurrence frequency, device state estimation using reaction process data becomes possible, and it becomes possible to achieve more efficient device maintenance and improved device reliability without the addition of any new parts.

MODES FOR CARRYING OUT THE INVENTION

Embodiments

Embodiment 1

Figure 1:
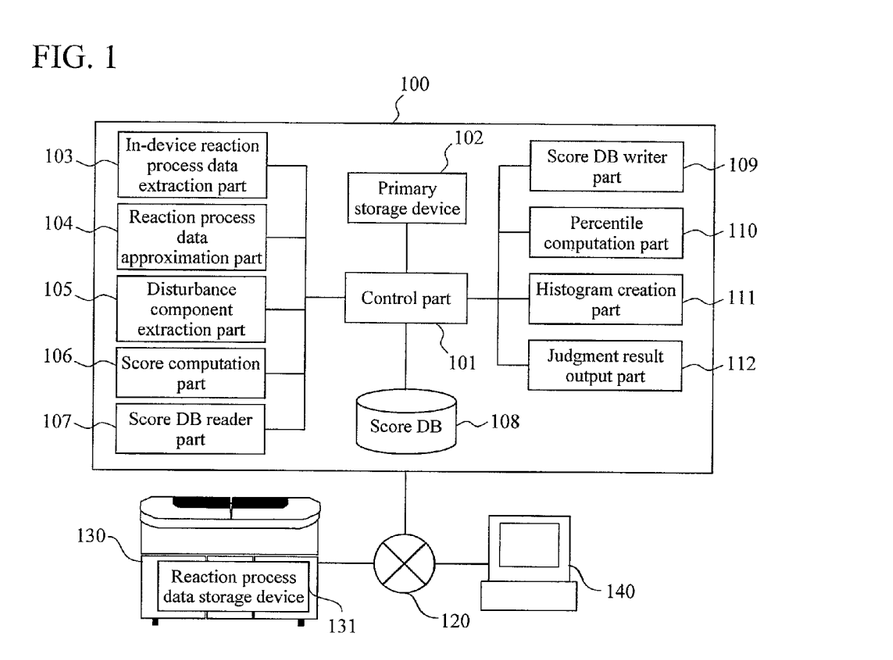
FIG. 1 shows a configurational diagram of a system for assisting judgment of abnormality as an embodiment of the present invention.

A configurational diagram of a system 100 for assisting judgment of abnormality as a first embodiment of the present invention is shown in FIG. 1.

The present system 100 comprises: a control part 101; a primary storage device 102; an in-device reaction process data extraction part 103; a reaction process data approximation part 104; a disturbance component extraction part 105; a score computation part 106; a score DB reader part 107; a score DB 108; a score DB writer part 109; a percentile computation part 110; a histogram creation part 111; and a judgment result output part 112.

Although the present system 100 is described in terms of hardware configuration, the functions of the present system 100 may also be configured with software.

The present system 100 is capable of communicating with an automatic analyzer 130 via a network 120. In addition, the present system 100 is capable of communicating with an input/output terminal 140 via the network 120.

Although the network 120 is assumed to be a network within a testing facility, it may also be a network within a medical facility having a testing department.

The automatic analyzer 130 stores reaction process data in a reaction process data storage device 131. In addition, the reaction process data stored in the reaction process data storage device 131 can be extracted by the in-device reaction process data extraction part 103 via the network 120. In addition, the reaction process data stored in the reaction process data storage device 131 can be viewed with the input/output terminal 140 via the network 120.

Although the automatic analyzer 130 is described as hardware that is separate from the present system 100, the configuration of the present system 100 may also be configured within the automatic analyzer 130.

While it is assumed that the reaction process data storage device 131 is configured within the automatic analyzer 130, the automatic analyzer 130 and the reaction process data storage device 131 may also be configured with separate hardware. In addition, the reaction process data storage device 131 may also be configured within the present system 100. In addition, the reaction process data storage device 131 may also be configured within the input/output terminal 140.

While information equipment such as a personal computer, etc., which has a keyboard, mouse, etc., as input functions, and a CRT display as an output function, is contemplated for the input/output terminal 140, it may also have other input/output functions. In addition, the input/output terminal 140 may also be a terminal equipped with a web browser function. In addition, although the input/output terminal 140 is described as hardware that is separate from the present system 100, the input/output functions of the input/output terminal 140 may also be incorporated into the present system 100. In addition, although the input/output terminal 140 is described as hardware that is separate from the automatic analyzer 130, the input/output functions of the input/output terminal 140 may also be incorporated into the automatic analyzer 130. In addition, although the input/output terminal 140 is assumed to be a personal computer, it may also be a laboratory information system.

In addition, although it is assumed that the user of the input/output terminal 140 is an operator of the automatic analyzer 130; such as a laboratory technician, etc., it may also be some other user, such as a person in charge of maintenance of the automatic analyzer 130, etc.

In addition, the present system 100, the automatic analyzer 130, and the input/output terminal 140 may also be configured as a single piece of hardware.

Figure 2:
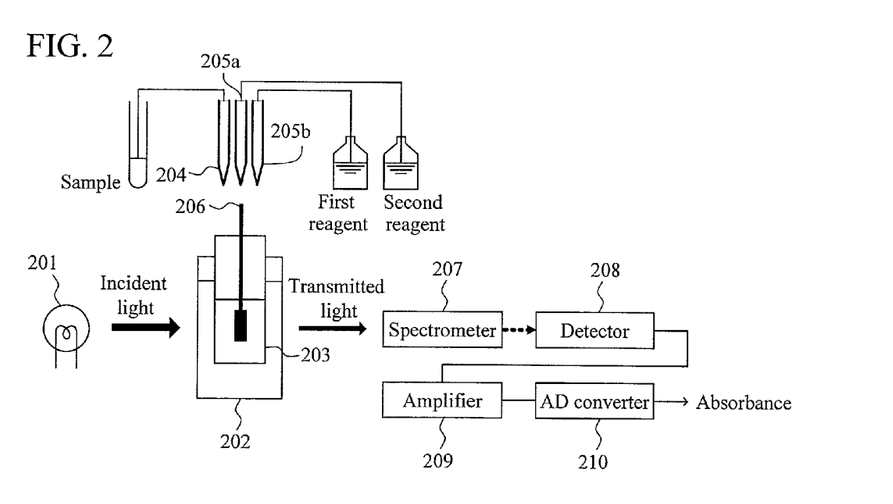
FIG. 2 shows a configurational diagram of an automatic analyzer.

A configurational diagram of the automatic analyzer 130 is shown in FIG. 2. The automatic analyzer 130 comprises: a light source lamp 201; a constant temperature bath 202; a cell 203; a sample dispenser nozzle 204; a first reagent dispenser nozzle 205a; a second reagent dispenser nozzle 205b; a stirring mechanism 206; a spectrometer 207; a detector 208; an amplifier 209; and an A/D convertor 210. During analysis, white light (all wavelengths) emitted from the light source lamp 201 travels through the cell 203 immersed in the constant temperature bath 202 to enter the spectrometer 207. A given single-wavelength component, which varies depending on the analysis item, is received by the detector 208, A/D converted at the A/D convertor 210 after amplification by the amplifier 209, and outputted as absorbance.

The cell is a reaction container. As a sample, a first reagent and a second reagent are respectively dispensed from the sample dispenser nozzle 204, the first reagent dispenser nozzle 205a and the second reagent dispenser nozzle 205b, and are stirred by the stirring mechanism 206, a chemical reaction takes place within the cell. By measuring absorbance (photometry) over time with respect to this chemical reaction, conversion into concentration and/or activity value of an analyte within the sample becomes possible.

Characteristic changes in absorbance that are appeared in reaction process data are described below.

In some cases, abnormalities may be appeared in the reaction process data due to bubbles, water deposits, or foreign substances within the constant temperature bath 202 or the cell 203 blocking the optical axis. Abnormalities that occur in such cases are appeared in the reaction process data of multiple wavelengths as temporary rises in absorbance (hereinafter referred to as jumps). In other words, when such jumps are frequently appeared in the reaction process data, it may be suspected that water deposits or foreign substances have entered the constant temperature bath 202 or the cell 203. Therefore, of the abnormal changes in absorbance manifested in the reaction process data, by detecting abnormalities caused by jumps, it is possible to narrow down the causes for the abnormalities, and allow for early discovery of device abnormality, that is, more efficient device maintenance and improved device reliability.

An object of the present invention is to automatically analyze the magnitudes of jumps from reaction process data, detect points where jumps are large, and present the occurrence frequency of jumps.

Figure 3:
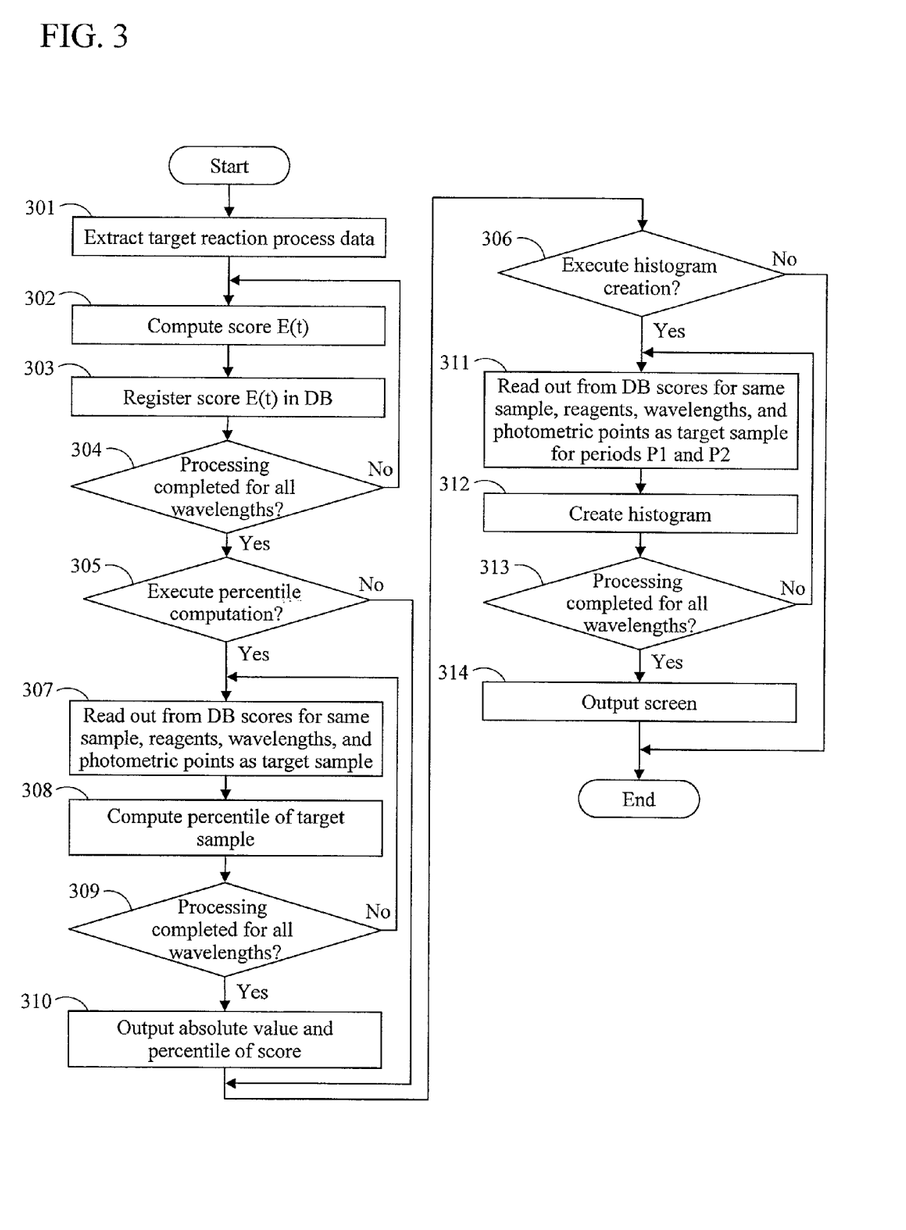
FIG. 3 shows a flowchart of a process for assisting judgment of abnormality in an embodiment of the present invention.

There is shown in FIG. 3 a flowchart 300 for a case of assisting judgment of abnormality through jumps based on reaction process data obtained by measuring a quality control sample.

First, the control part 101 activates the in-device reaction process data extraction part 103, and executes step 301 wherein reaction process data of wavelength λ, which is the target for processing, is extracted from the reaction process data stored in the reaction process data storage device 131 and stored in the primary storage device 102.

Next, the control part 101 activates the score computation part 106, and executes step 302 wherein a score representing the magnitude of a jump is computed per photometric time point from the reaction process data. The score is computed with Equation (1). Equation (1) indicates that the score of a jump at the photometric time point at time t is defined as the smaller of the absorbance differences relative to the preceding and succeeding t−1 and t+1, respectively. Thus, it is possible to quantify a momentary rise in absorbance, which is characteristic of jumps, that is, a rise in absorbance only at a single point.

$$E(t)=\min((A(t)-A(t-1)),(A(t)-A(t+1))) \quad (1)$$

Figure 4:
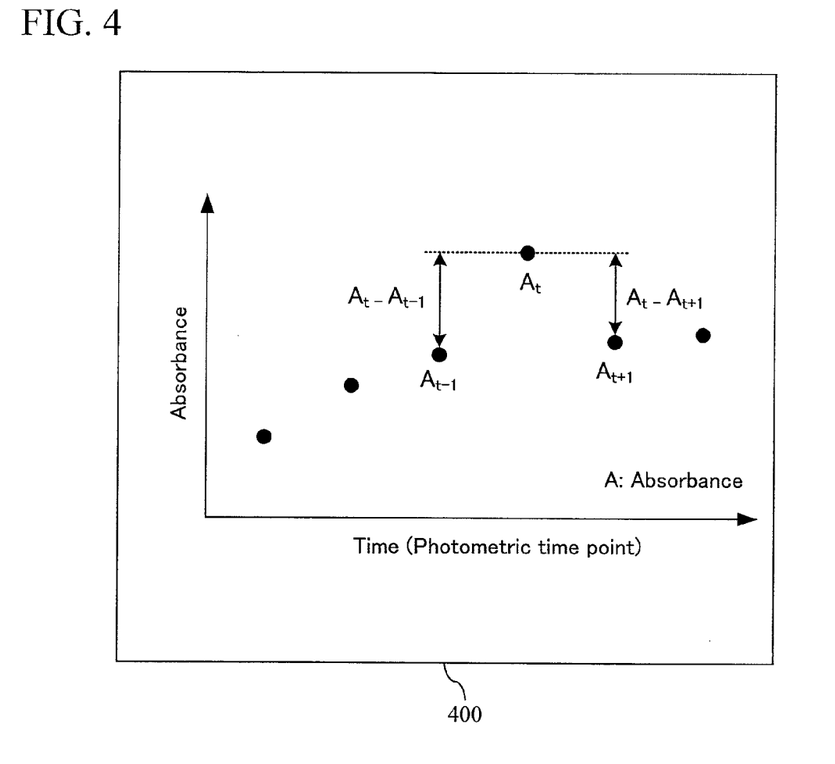
FIG. 4 shows a score computation example upon execution of step 302.

Example 400 in which Equation (1) is applied to jumps in the reaction process data is shown in FIG. 4. In example 400, $A_t$ represents the absorbance at time t, and there is an occurrence of a jump in absorbance at time t. When Equation (1) is applied to $A_t$, the smaller of the differences between $A_t$ and $A_{t-1}$, and between $A_t$ and $A_{t+1}$ is computed as the score. If there is an occurrence of a jump, since there would be significant discrepancies in absorbance relative to $A_{t-1}$ and $A_{t+1}$, respectively, the score would be greater than neighboring scores.

Next, the control part 101 activates the score DB writer part 109, and executes step 303 wherein the score computed with the sample currently being processed is registered in the DB.

Figure 5:
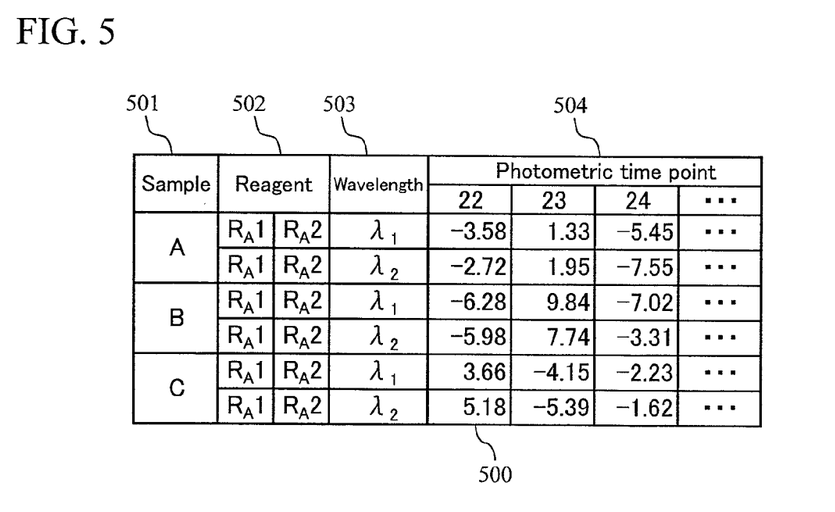
FIG. 5 shows a data table example of a score DB.

Example 500 of a score DB is shown in FIG. 5. The score DB 108 comprises: a field 501 for storing sample IDs for identifying the kind of a sample; a field 502 for storing reagent IDs for identifying the kinds of a first reagent and a second reagent; a field 503 for storing the kinds of the wavelengths that were used in the analysis; and a field 504 for storing scores computed for the respective photometric time points. In example 500, it is shown that for the sample identified by the sample ID "A" and which has been analyzed using reagents "$R_A1$" and "$R_A2$" and at wavelength "$λ_1$," the score is "−3.58" at photometric time point 22, "1.33" at photometric time point 23, and "−5.45" at photometric time point 24.

Next, the control part 101 executes step 304 wherein it is determined if processing has been performed with respect to all wavelengths that are to be processed.

If in step 304, it is determined that processing has not been completed with respect to all wavelengths that are to be processed, the control part 101 activates the in-device reaction process data extraction part 103 and executes step 302 to step 303 with respect to the wavelengths for which processing has not been completed. Data analysis that makes use of the characteristic where jumps caused by bubbles, water deposits, or foreign substances occur at a plurality of wavelengths thus becomes possible.

Through step 301 to step 304 above, it becomes possible to quantify by how much the absorbance at a target photometric time point rises relative to the absorbance at neighboring photometric time points.

Next, there is explained a process for assisting judgment of jumps by computing the relative magnitudes of jumps using the scores.

First, the control part 101 executes step 305 wherein it is determined whether or not to execute a process of computing the relative magnitudes of jumps. If the process of computing the relative magnitudes of jumps is not to be performed, step 306 is executed. Step 306 will be described later.

If the process of computing the relative magnitudes of jumps is to be performed, the control part 101 activates the score DB reader part 107, and executes step 307 wherein the scores for the same sample, reagents and wavelengths as the target are read out from the score DB 108.

Next, the control part 101 activates the percentile computation part 110, and executes step 308 wherein the percentiles of the scores of the target sample and photometric time points with respect to the scores at the same photometric time points for the read out wavelength are computed. The relative magnitudes of the jumps at the respective photometric time points of the target sample are thus indicated.

Figure 6:
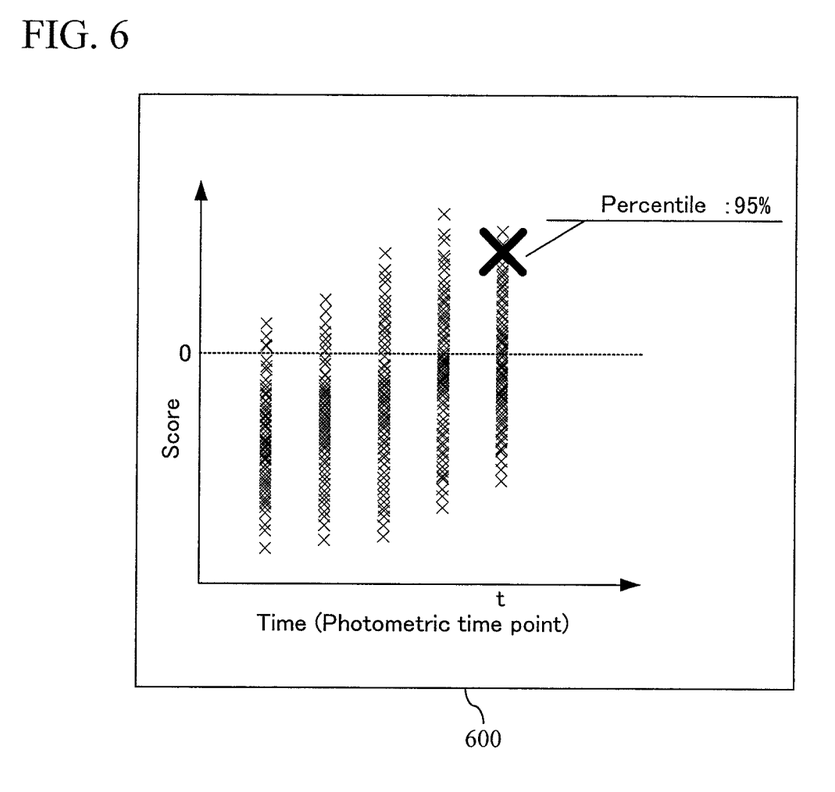
FIG. 6 shows examples of scores at various photometric time points and a computed percentile.

Example 600 of the scores at each photometric time point and a computed percentile is shown in FIG. 6. In example 600, photometric time point and score magnitude of the scores read out from the DB are plotted, and it is shown that the percentile of the target sample at time t is 95%. In addition, in example 600, it can also be observed that the average values and variance of the score distributions vary from photometric time point to photometric time point. By indicating the relative magnitudes of the scores, it is possible to assist judgment of jumps wherein the influence of differences in the distributions at the respective photometric time points is taken into account.

Next, the control part 101 executes step 309 wherein it is determined if processing has been performed with respect to all wavelengths that are to be processed. Reaction process data analysis that makes use of the characteristic of jumps which is that jumps occur at all wavelengths thus becomes possible. If it is determined that processing has not been completed with respect to all wavelengths that are to be processed, the control part 101 executes steps 307 and 308 with respect to the wavelengths concerned.

Next, the control part 101 activates the judgment result output part 112, and executes step 310 wherein the absolute values and percentiles of the scores of each wavelength are outputted.

Figure 7:
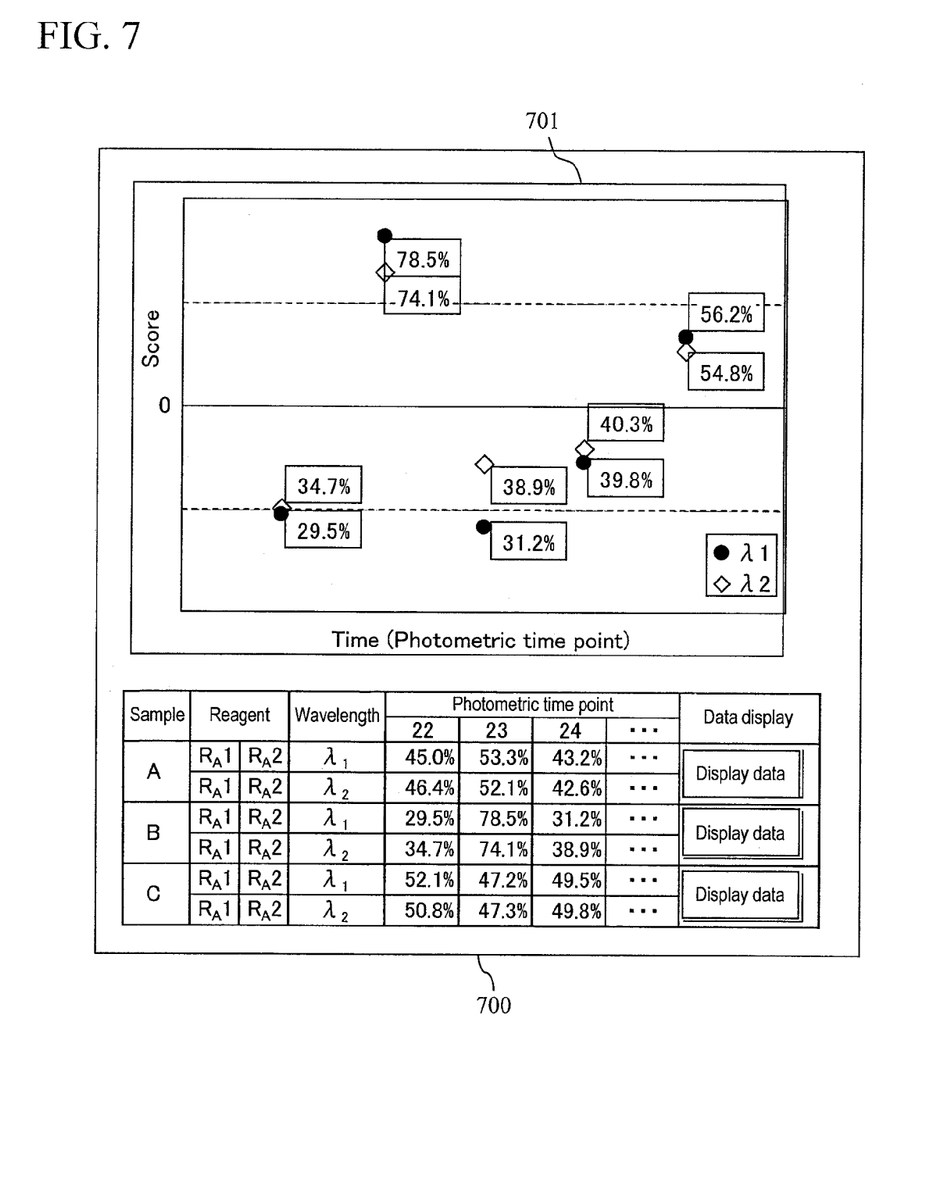
FIG. 7 shows a screen example of an input/output terminal after execution of step 310.

A screen example of the input/output terminal 140 when score rank results are outputted is shown at 700 in FIG. 7. In screen example 700, percentiles, which indicate the relative magnitudes of the scores, are displayed in a graph 701 indicating the absolute magnitudes of the scores. A laboratory technician is thus able to know if a time point with a large score is specifically large in comparison to the results for other samples at the same photometric time point. On the other hand, even if a score is relatively smaller than at other photometric time points, it is possible to examine if it is specifically large in comparison to the results for other samples at the same photometric time point. It is thus possible to make it easier to determine whether there are any occurrences of jumps in the target sample.

By computing the relative magnitudes of jumps through the procedure above, it becomes possible to assist the judgment of jumps.

Next, after step 310 is executed, or if it is determined in step 305 that the process of indicating, in relative terms, the magnitudes of the jumps is not to be executed, step 306 is executed wherein it is determined if a process of presenting changes in the occurrence frequency of jumps over time is to be executed. If the process of presenting changes in the occurrence frequency of jumps over time is not to be performed, the present process is terminated.

If the process of presenting changes in the occurrence frequency of jumps over time is to be executed, the control part 101 activates the score DB reader part 107, and executes step 311 wherein scores for the same sample, reagents and wavelengths during period P1, which serves as a reference for comparison, and period P2, which is the current period, are read out. Periods P1 and P2 may be, for example, all samples from month x day x to month y day y, all samples from xx:xx to yy:yy, all samples with sample IDs xx to yy, etc.

Next, the control part 101 activates the histogram creation part 111, and executes step 312 wherein histograms of score magnitudes per wavelength and per photometric time point are created respectively for periods P1 and P2. It is thus possible to obtain a score distribution for each period.

Next, the control part 101 executes step 313 wherein it is determined if processing has been performed with respect to all wavelengths that are to be processed. Reaction process data analysis that makes use of the characteristic of jumps which is that jumps occur at all wavelengths thus becomes possible. If it is determined that processing has not been completed with respect to all wavelengths that are to be processed, the control part 101 executes steps 311 and 312 with respect to the wavelengths concerned.

Next, the control part activates the result output part 112, and performs step 314 wherein histograms for periods P1 and P2 are simultaneously outputted.

Figure 8:
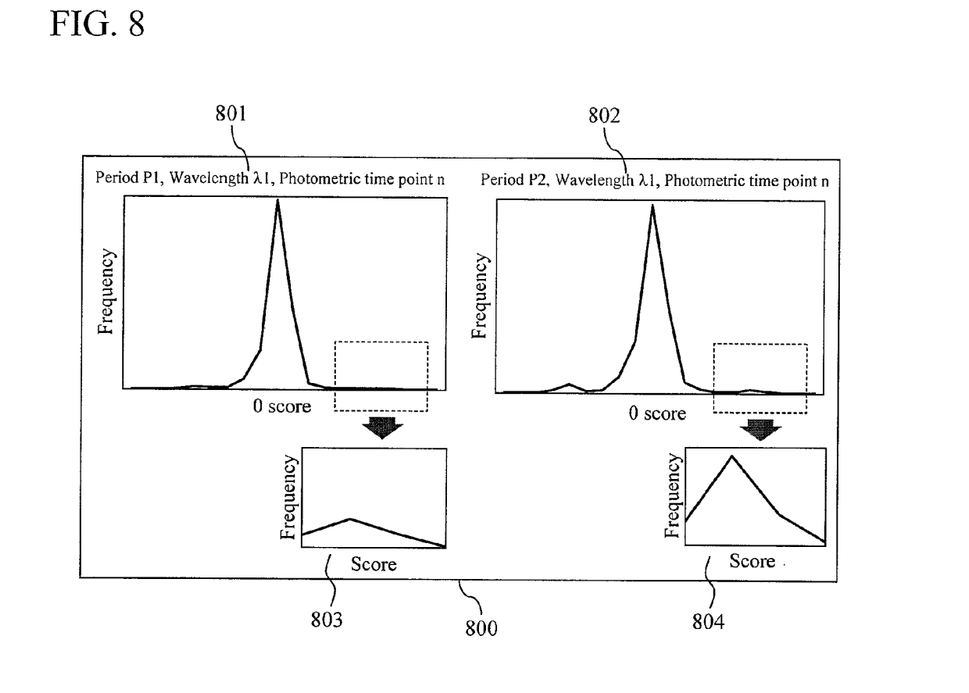
FIG. 8 shows a screen example of an input/output terminal after execution of step 314.

Screen example 800 of the input/output terminal 140 for a case where two histograms are displayed is shown in FIG. 8. In screen example 800, histogram 801 for period P1 and histogram 802 for period P2 are displayed in such a manner that their peak heights are aligned. In addition, in order to display the frequency at a photometric time point with a large score in a manner that is easy to understand, histogram 803, which is an enlargement of a portion of histogram 801, and histogram 804, which is an enlargement of a portion of histogram 802, are displayed, and ranges are set appropriately so as to enable observation of differences in frequency at a glance. Thus, score distributions can be compared between periods P1 and P2, and it is possible to examine if the jump occurrence frequency is greater or less. If a difference in occurrence frequency is observed, and there are currently more jumps, device abnormalities such as water deposits or foreign substances having entered the constant temperature bath 202 or the cell 203 may be suspected. As a laboratory technician would be able to determine with ease through this screen if there are any significant differences in the occurrence frequency of large jumps, it is possible to perform device maintenance at suitable timing.

By thus analyzing reaction process data through steps 301 to 314, it becomes possible to assist judgment of abnormality based on jumps.

Although in the present embodiment, it is mentioned that histograms are created per wavelength and per photometric time point in step 312, histograms may be created without differentiating by wavelength or photometric time point. Thus, it would be possible to examine frequency distributions of a period of interest in a single histogram, and a laboratory technician would be able to examine the data in a simpler manner.

In addition, although it is mentioned that a histogram of score magnitude is created in step 312, a histogram may also be created from differences between scores and the average value of the scores instead of from score magnitudes. Thus, influences of bias per wavelength and photometric time point are removed, and it is possible to draw fairer comparisons when a histogram is created without differentiating by wavelength or photometric time point.

In addition, although it is mentioned that the peak heights of the two histograms 801 and 802 are aligned in step 314, the heights of certain data intervals that are to serve as references may be aligned instead. This would make the difference clearly visible when the data intervals in which peaks are present are different.

Embodiment 2

Next, the second embodiment of the present invention is described. The present embodiment is one in which there has been added a process of extracting an absorbance change component caused by disturbances by removing from the reaction process data an absorbance change component caused by the reaction. The other features and processes are generally the same as those in the first embodiment.

Figure 9:
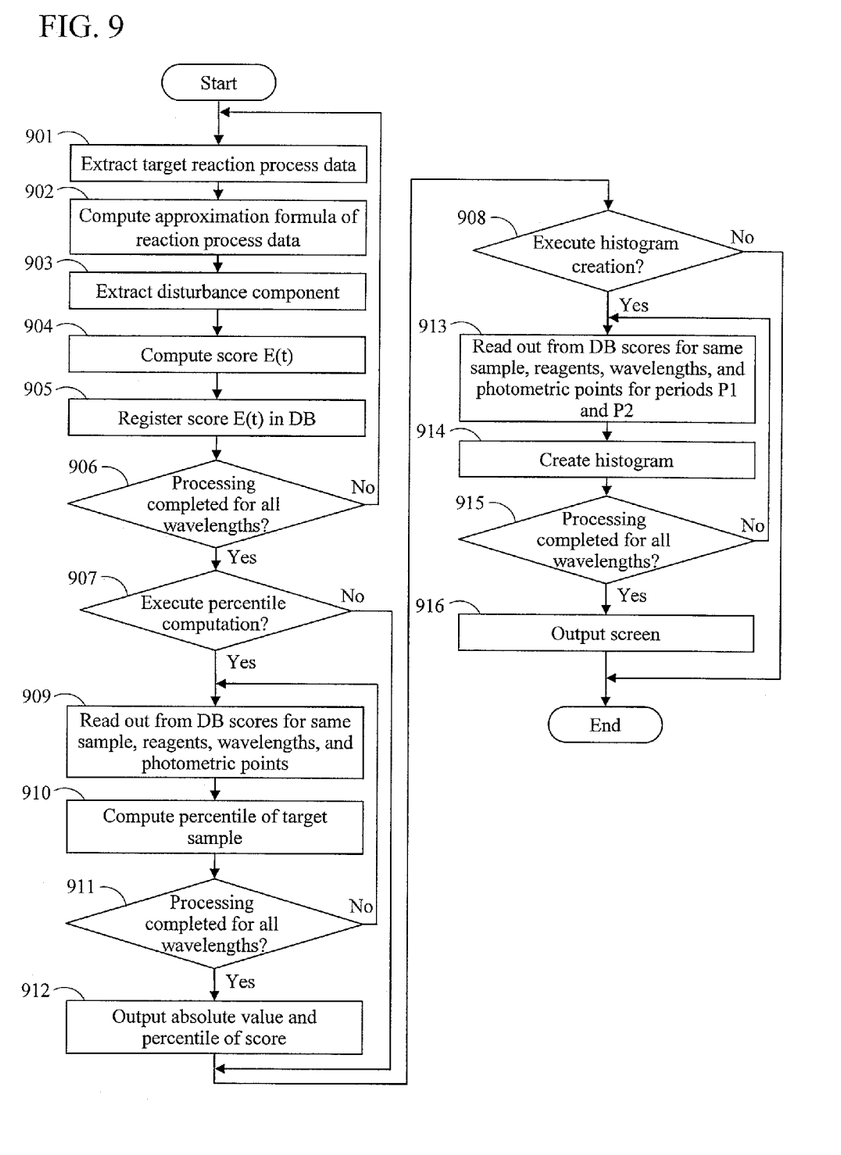
FIG. 9 shows a flowchart of a process for assisting judgment of abnormality including a disturbance component extraction process.

There is shown in FIG. 9 a flowchart for quantifying the magnitude of a jump based on reaction process data that is obtained by measuring a quality control sample.

First, step 901, which is the same as step 301 mentioned above, is executed.

Next, the control part 101 activates the reaction process data approximation part 104, and executes step 902 wherein an approximate function for the reaction process data is computed. For example, assuming Equation (2) is a model of the approximate function, approximate parameters k, A0 and A1 are computed, and an approximate value is found.

$$A(t)=A0+A1(1-e^{-kt}) \qquad (2)$$

where k, A0, and A1 are approximate parameters representing the reaction rate constant, the initial absorbance at the time when reaction starts, and the concentration of a component of interest, respectively, and t, A(t), and e represent time, the absorbance at a photometric time point at time t, and the base of the natural logarithm, respectively.

Figure 10:
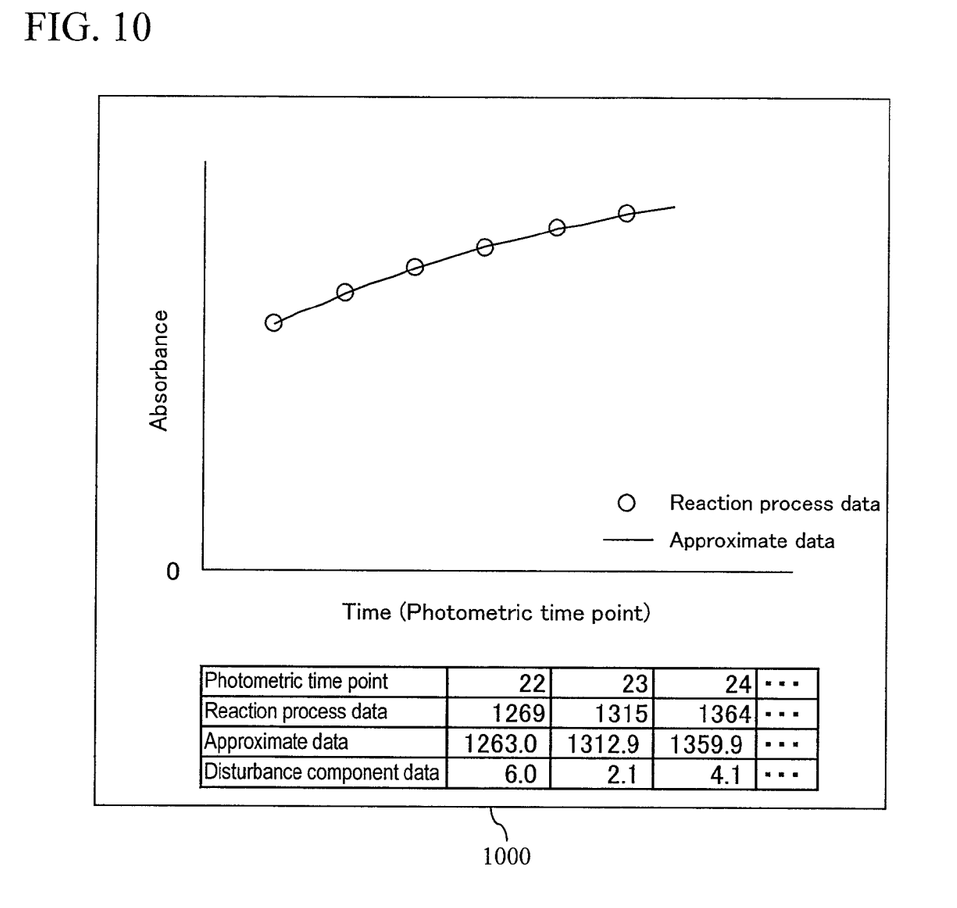
FIG. 10 shows examples of reaction process data and approximate values thereof after execution of step 902.

Example 1000 of reaction process data after step 902 has been executed is shown in FIG. 10. In example 1000, there is shown how fitting by curve approximation has been performed with respect to the reaction process data.

Next, the control part 101 activates the disturbance component extraction part 105, and executes step 903 wherein a disturbance component of the reaction is extracted by computing the difference between the reaction process data and an approximate value. Thus, the absorbance change component of the reaction process data caused by the reaction is removed, changes in absorbance caused by disturbances become clearer, and it becomes possible to perform highly accurate judgment of abnormality. In addition, although, in some cases, significant differences caused by the reaction are observed in absorbance distributions per wavelength or photometric time point with respect to the reaction process data, those differences can be reduced by extracting the disturbance component. This makes it possible to compare scores between wavelengths and between photometric time points.

Figure 11:
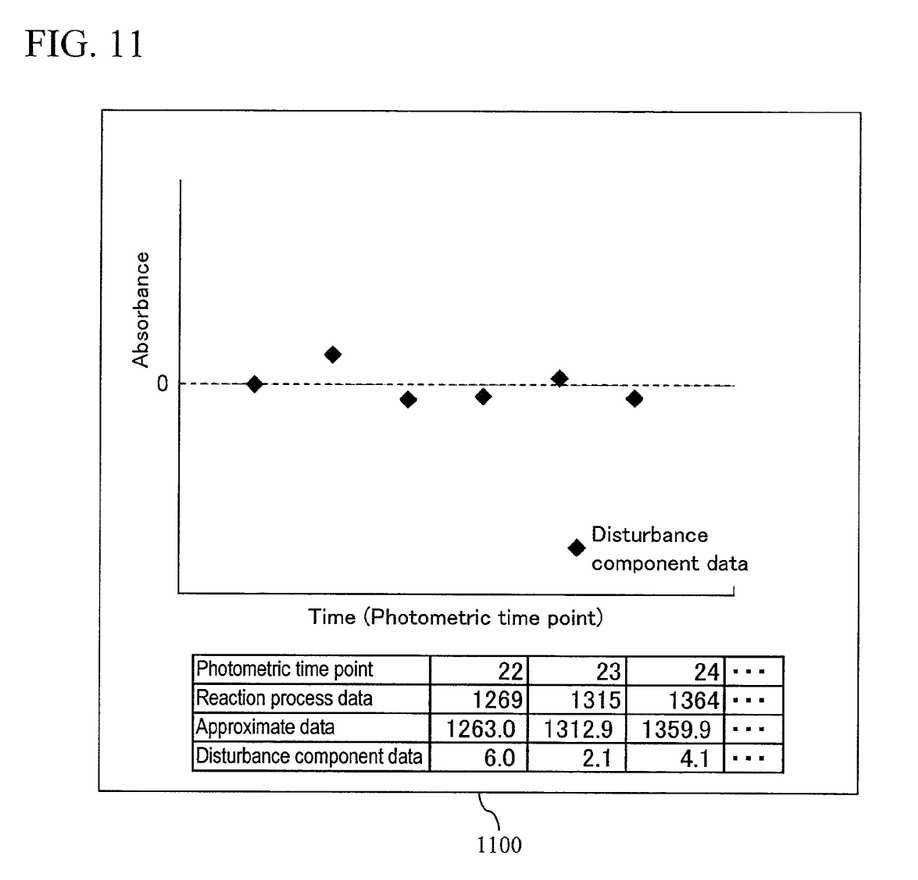
FIG. 11 shows examples of disturbance components of reaction process data after execution of step 903.

Example 1100 of disturbance component data after step 903 has been executed is shown in FIG. 11. In example 1100, it is shown that the absorbance change component caused by the reaction is removed, and that changes in absorbance caused by disturbance are removed.

Next, the control part 101 activates the score computation part 106, and executes step 904 wherein a score representing the magnitude of a jump is computed per photometric time point based on disturbance component data. Scores are computed with Equation (3). Equation (3) is an equation similar to Equation (1), but instead of using the difference in absorbance for the score, the disturbance component computed in step 903 is used. In Equation (3), D is the disturbance component.

$$E(t)=\min((D(t)-D(t-1)),(D(t)-D(t+1))) \quad (3)$$

Through step 901 to step 904 above, it becomes possible to quantify, based on the disturbance component of absorbance change, by how much the absorbance at the target photometric time points has risen relative to the absorbance at neighboring photometric time points.

With respect to step 905 to step 916, since they are to the same as step 303 to step 314 mentioned above, descriptions are omitted.

Through steps 901 to 916 above, it becomes possible to accurately assist the judgment of abnormality based on jumps by analyzing the absorbance change component caused by disturbance extracted from the reaction process data.

Although in the present embodiment it is mentioned that approximation modeled on Equation (2) is performed in step 902, the approximation method may use any model such as polynomial approximation, Taylor expansion, etc. This makes it possible to select a suitable model equation in accordance with the reaction process data, and computation of a more accurate score becomes possible. However, in this case, the parameters to be derived will be different.

In addition, although percentiles are computed per wavelength and per photometric time point in step 910, percentiles may also be computed without differentiating by wavelength or photometric time point. In addition, the average value or median value of the computed percentiles per wavelength may be taken to be a representative value at that photometric time point. This reduces the number of graphs showing the percentiles of one sample, making the data examining operation easier for laboratory technicians.

In addition, although it is mentioned that a histogram is created per wavelength and photometric time point in step 914, a histogram may also be created without differentiating by wavelength or photometric time point. This makes it possible to examine frequency distributions of a target period in one histogram, making it possible for laboratory technicians to examine data in a simpler manner.

In addition, although it is mentioned that a histogram of score magnitudes is created in step 914, a histogram may also be created from, instead of score magnitudes, differences between scores and the average value of the scores. As a result, influences of bias per wavelength and photometric time point are removed, allowing for a fairer comparison in cases where a histogram is created without differentiating by wavelength or photometric time point.

In addition, although it is mentioned that the peak heights of the two histograms 801 and 802 are aligned in step 916, the heights of certain data intervals that are to serve as references may be aligned instead. This would make the difference clearly visible when the data intervals in which peaks are present are different.

Embodiment 3

Figure 12:
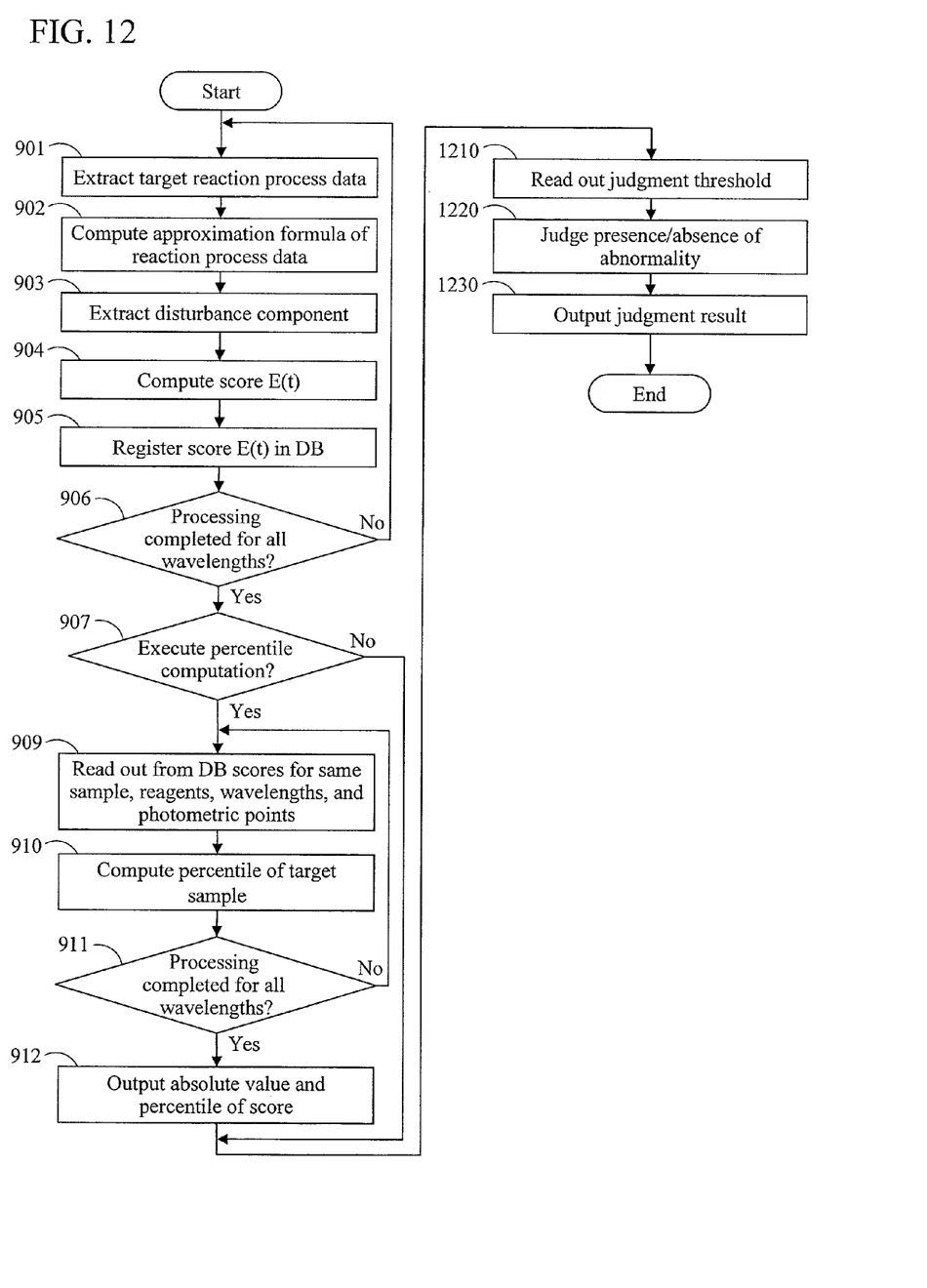
FIG. 12 is a diagram showing a process flow of a third embodiment of the present invention.

Next, the third embodiment of the present invention is described. The configuration of the device is the same as in Embodiments 1 and 2. FIG. 12 shows a process flow for judging the presence/absence of an abnormality in the reaction process data in the present embodiment. It is noted that process steps that perform the same processes as those in FIG. 9 describing the process flow used in the description for Embodiment 2 are designated with the same symbols.

Since the processes across process steps 901-912 are the same as the process steps of the same reference numerals in FIG. 9 with respect to Embodiment 3, descriptions will be omitted. In addition, the processes of process steps 1210-1230 discussed below are performed at the control part. The determination as to whether or not to compute the percentile value in process step 907 is set in advance by the user. Percentile computation may be executed with respect to all items, or with respect to only a portion of the items. In addition, the settings may also be such that percentile is not executed with respect to any of the items.

In process step 1210, a judgment threshold for judging abnormalities is read out. A pre-defined value is stored for the judgment threshold. The value may be stored in the score DB 108, or it may be held within the control part 101. In addition, the configuration may be such that the value can be changed by the user. With respect to the threshold, different values may also be set for each test item or reagent. In addition, the same value may be used at each photometric time point, or a different value may be used at each photometric time point.

With respect to items for which it has been determined that percentile is to be executed in step 907, it is possible to define with ease, by way of a relative value, how much of a deviation, as a judgment threshold, relative to a distribution of past score values is to be judged an abnormality. For example, if score values in the top and bottom 1% from a distribution of past data are to be judged abnormal, two kinds of thresholds, namely 1% and 99%, are set for the percentile value.

In process step 1220, the score value computed in process step 904 or the percentile value computed in process step 910 is compared with the judgment threshold read out in process step 1210 to judge the presence/absence of an abnormality. For example, where, as mentioned above, two kinds of judgment thresholds, namely 1% and 99%, have been set, if the percentile value computed in process step 910 is 1% or less, or 99% or greater, it is judged as being abnormal, whereas it is otherwise judged as being normal.

In process step 1230, the judgment result in process step 1220 is outputted to the judgment result output part 112.

In the process flow shown in FIG. 12, a disturbance component extraction process is performed in process steps 902 and 903. However, as in the first embodiment, a configuration in which no disturbance component extraction is performed is also possible. In this case, since a computation process for an approximation equation, which takes time, is not performed, it is possible to speed up the process.

According to the third embodiment discussed above, by using a score value based on a difference value relative to a neighboring photometric time point, it is possible to accurately detect abnormal data such as data in which only a single point in the reaction process data exhibits abnormal fluctuation. In addition, by using a percentile value converted from a score value, it is possible to define with ease, by way of a relative value, by how much data is to deviate from past data to be judged abnormal. In addition, by extracting a disturbance component using an approximation equation, it becomes possible to detect an abnormal fluctuation component more accurately.

DESCRIPTION OF SYMBOLS

100 System for assisting judgment of abnormality
101 Control part
102 Primary storage device
103 In-device reaction process data extraction part
104 Reaction process data approximation part
105 Disturbance extraction part
106 Score computation part
107 Score DB reader part
108 Score DB
109 Score DB writer part
110 Percentile computation part
111 Histogram creation part
113 Judgment result output part
120 Network within a testing facility
130 Automatic analyzer
131 Reaction process data storage device
140 Input/output terminal
201 Light source lamp
202 Constant temperature bath
203 Cell
204 Sample dispenser nozzle
205a First reagent dispenser nozzle
205b Second reagent dispenser nozzle
206 Stirring mechanism
207 Spectrometer
208 Detector
209 Amplifier
210 A/D converter

The invention claimed is:

1. An automatic analyzer that measures the concentration or activity value of a component of interest in a sample, the automatic analyzer comprising:
a reaction container to contain a mixture in which the sample and one or more kinds of reagents are mixed;
a light source to emit a plurality of wavelengths of light through the reaction container;
a detector to detect time series data of photometric values obtained by optically measuring the plurality of wavelengths of light emitted through the reaction container;
an indicator computation unit configured to calculate, at each time point t of the time series data, a first difference between the value of the time series data at the time point t and at a preceding time point t−1 and a second difference between the value of the time series data at the time point t and a succeeding time point t+1, the indicator computation unit configured to compare an absolute value of the first difference with an absolute value of the second difference, and the indicator computation unit configured to use as an indicator a smaller value of the absolute value of the first difference and the absolute value of the second difference;
wherein a presence or an absence of an abnormality is judged based on comparing a value of the indicator to a threshold, wherein the indicator being greater than the threshold indicates the presence of the abnormality, and the indicator being less than the threshold indicates the absence of the abnormality.

2. An automatic analyzer according to claim 1, further comprising:
a relative indicator computation unit configured to calculate a relative distance between a center of a distribution of a plurality of the indicators computed with respect to samples measured in the past, and the indicator computed with respect to a newly measured sample.

3. An automatic analyzer according to claim 1, further comprising:
a reaction change component estimation unit configured to approximate the time series data with a function, and to use a value approximated by the function as a photometric value change component caused by a chemical reaction; and
a disturbance change component extraction unit configured to compute a difference between the time series data and an estimated value obtained at the reaction change component estimation unit, and to extract time series data of change components caused by a disturbance.

4. An automatic analyzer according to claim 1, further comprising:
an indicator display unit configured to simultaneously display a value computed by the indicator computation unit and a value computed by the relative indicator computation unit.

5. An automatic analyzer according to claim 1, further comprising:
a unit configured to judge a presence or an absence of an abnormality, based on a value computed by the indicator computation unit.

6. An automatic analyzer according to claim 1, further comprising:
a relative indicator computation unit configured to calculate a relative distance between a center of a distribution of a plurality of the indicators computed with respect to samples measured in the past, and the indicator computed with respect to a newly measured sample; and
a unit configured to judge a presence or an absence of an abnormality based on the relative indicator.

* * * * *